United States Patent
Camarero Díez et al.

(10) Patent No.: US 11,865,230 B2
(45) Date of Patent: Jan. 9, 2024

(54) VOLATILE SUBSTANCE DIFFUSER

(71) Applicant: ZOBELE HOLDING S.P.A., Trento (IT)

(72) Inventors: Roberto Camarero Díez, Barcelona (ES); Dominic Doyle, Barcelona (ES)

(73) Assignee: Zobele Holding S.P.A., Trento (IT)

( * ) Notice: Subject to any disclaimer, the term of this patent is extended or adjusted under 35 U.S.C. 154(b) by 120 days.

(21) Appl. No.: 16/958,208

(22) PCT Filed: Dec. 26, 2018

(86) PCT No.: PCT/EP2018/086883
§ 371 (c)(1),
(2) Date: Jun. 26, 2020

(87) PCT Pub. No.: WO2019/129788
PCT Pub. Date: Jul. 4, 2019

(65) Prior Publication Data
US 2021/0069367 A1    Mar. 11, 2021

(30) Foreign Application Priority Data
Dec. 27, 2017 (ES) .................. ES201731472

(51) Int. Cl.
*A61L 9/12*     (2006.01)
*B65D 73/00*    (2006.01)
*A01M 1/20*     (2006.01)

(52) U.S. Cl.
CPC ............ *A61L 9/12* (2013.01); *B65D 73/0078* (2013.01); *A01M 1/2055* (2013.01); *A61L 2209/15* (2013.01)

(58) Field of Classification Search
CPC .................. A61L 9/12; A61L 2209/15
(Continued)

(56) References Cited

U.S. PATENT DOCUMENTS

| | | | | |
|---|---|---|---|---|
| 2,991,578 A | * | 7/1961 | Messina | B65D 5/5206 40/750 |
| 4,244,511 A | * | 1/1981 | Coleman | B65D 27/14 229/92.7 |

(Continued)

FOREIGN PATENT DOCUMENTS

| | | |
|---|---|---|
| GB | 484 035 A | 4/1938 |
| WO | 2002/007512 A1 | 1/2002 |
| WO | 2014028682 A1 | 2/2014 |

OTHER PUBLICATIONS

International Search Report received for PCT Patent Application No. PCT/EP2018/086883 dated Mar. 21, 2019, 3 page.
(Continued)

*Primary Examiner* — Jason J Boeckmann
(74) *Attorney, Agent, or Firm* — Amster, Rothstein & Ebenstein LLP

(57) ABSTRACT

The present invention relates to a volatile substance diffuser, where said diffuser comprises a reservoir (10) containing the volatile substances, characterized in that it is formed from a sheet (11) provided with a plurality of fold lines, said sheet (11) comprising a first face (1) on which said reservoir (10) is fixed; a second face (2) which supports the diffuser upright in a use position together with said first face (1); and a third face (3) provided with a hole (12) for hanging the diffuser. The present invention allows providing a volatile substance diffuser which prevents using a container housing said diffuser.

10 Claims, 4 Drawing Sheets

(58) Field of Classification Search
USPC .............................................. 239/34, 54, 57
See application file for complete search history.

(56) References Cited

U.S. PATENT DOCUMENTS

| | | | |
|---|---|---|---|
| 6,643,967 B1 * | 11/2003 | Bloom ................. | A47G 1/0616 40/750 |
| 2006/0283076 A1 | 12/2006 | Chambers et al. | |
| 2007/0194368 A1 | 8/2007 | Caserta et al. | |

OTHER PUBLICATIONS

Written Opinion received for PCT Patent Application No. PCT/EP2018/086883, 5 page.

\* cited by examiner

VOLATILE SUBSTANCE DIFFUSER

This application is a National Stage entry under 35 U.S.C. 371 of International Patent Application No. PCT/EP2018/086883, filed on Dec. 26, 2018, which claims priority from Spanish Patent Application No. P201731472, filed Dec. 27, 2017, the entire contents of each of which are incorporated by reference herein.

FIELD

The present invention relates to a volatile substance diffuser, the body of which is formed from a sheet provided with fold lines.

BACKGROUND OF THE INVENTION

Volatile substance diffusers are used as air fresheners or insecticides, such that the volatile substances are diffused into the surrounding area, providing a fragrance.

In these diffusers, the volatile substances are contained in a reservoir, which is opened when the diffuser is used for the first time.

To sell the diffuser, it is usually placed in a suspended state in a display, and to that end a hole must be provided so as to allow the diffuser to hang. This is achieved by placing the diffuser inside a container, usually a plastic container, which houses the diffuser and is provided with a lug with this hole for hanging said container for display.

Placing the diffuser inside a container evidently raises the sale price of the diffuser, which is a drawback, taking into account that the price of diffusers of this type is lower, so any additional cost has a direct effect on the success of product sales.

Therefore, an objective of the present invention is to provide a volatile substance diffuser which prevents the use of a container housing said diffuser, with the subsequent savings in the sale price, and which likewise allows the diffuser to be hung in a point of sale display.

SUMMARY OF THE INVENTION

The mentioned drawbacks are solved with the volatile substance diffuser of the invention, while having other advantages that will be described below.

The volatile substance diffuser according to the present invention comprises a reservoir containing the volatile substances, and is characterized in that it is formed from a sheet provided with a plurality of fold lines, said sheet comprising:

a first face on which said reservoir is fixed;
a second face which supports the diffuser upright in a use position together with said first face; and
a third face provided with a hole for hanging the diffuser.

As a result of this feature, it is the volatile substance diffuser itself that can be hung in a display, without having to use an independent container, with the subsequent savings in the cost of the volatile substance diffuser.

The faces of said sheet can advantageously be folded in a storage position and unfolded in the use position.

Preferably, said sheet also comprises a fourth face, which also supports the diffuser upright in a use position.

According to a first embodiment, said sheet also comprises a base face which forms the base of the diffuser in the use position.

Furthermore, the first and second faces may further comprise respective flaps which are coupled to one another when the diffuser is placed in the use position.

According to said first embodiment, said base face is arranged in a centered position in said sheet and has a square or rectangular shape, said first to fourth faces extending from the sides of said base face.

According to a second embodiment, the sheet may also comprise a cover face, which is folded over the third face in the storage position.

In this second embodiment, said first, second, and fourth faces are placed next to one another, and said third face is separable from the rest of the sheet when the diffuser is placed in the use position. Furthermore, said cover face is attached by means of a fold line to only said third face.

Advantageously, said reservoir comprises a separable sealing band which is removed before the first use of the diffuser, and said sheet is made of cardboard.

BRIEF DESCRIPTION OF THE DRAWINGS

To better understand what has been set forth, drawings in which a practical embodiment is schematically shown only by way of non-limiting example are attached.

DESCRIPTION OF A PREFERRED EMBODIMENT

Figure 1:
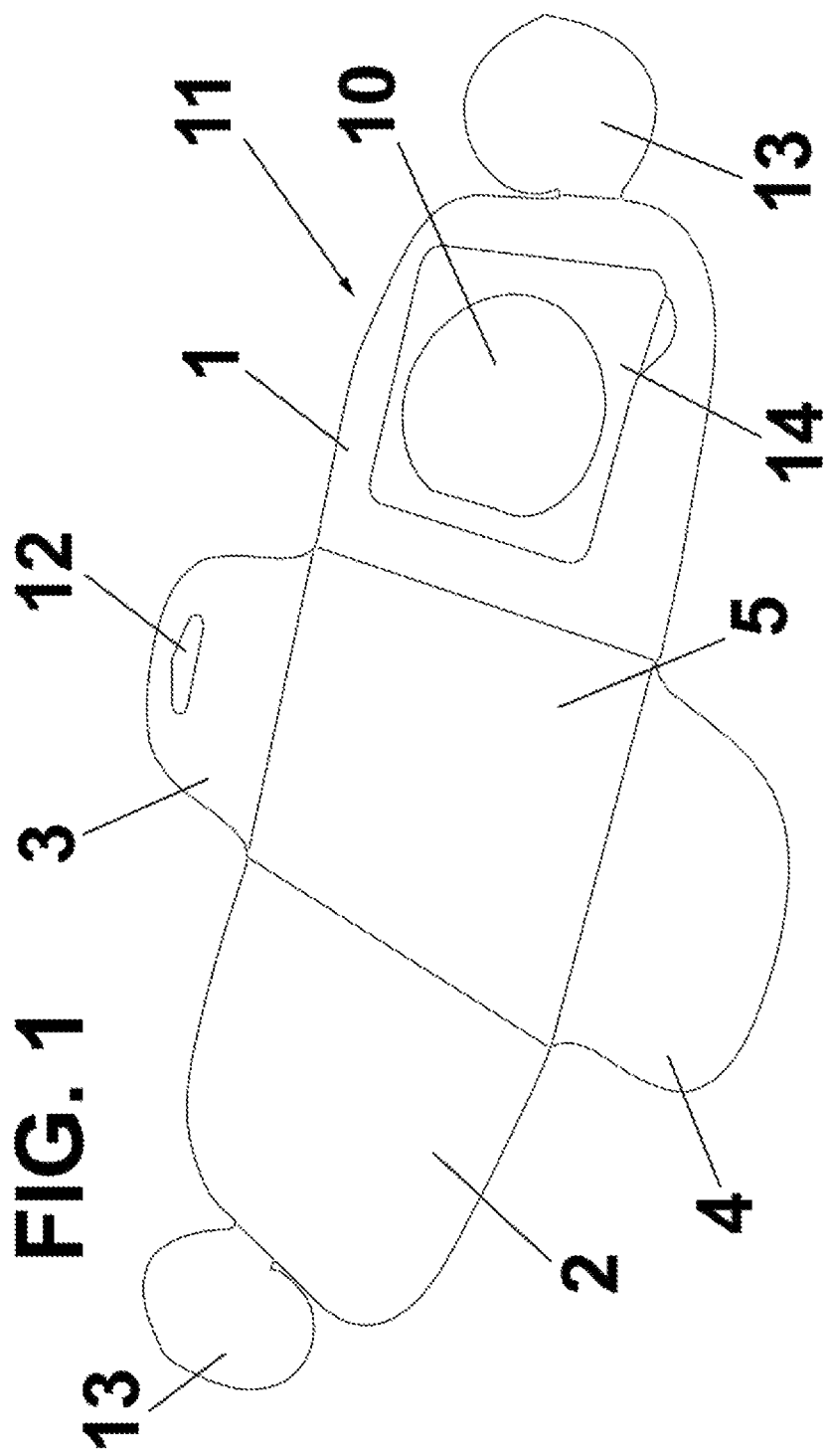
FIG. 1 is a perspective view of the unfolded sheet forming the volatile substance diffuser of the present invention, according to a first embodiment.
Figure 2:
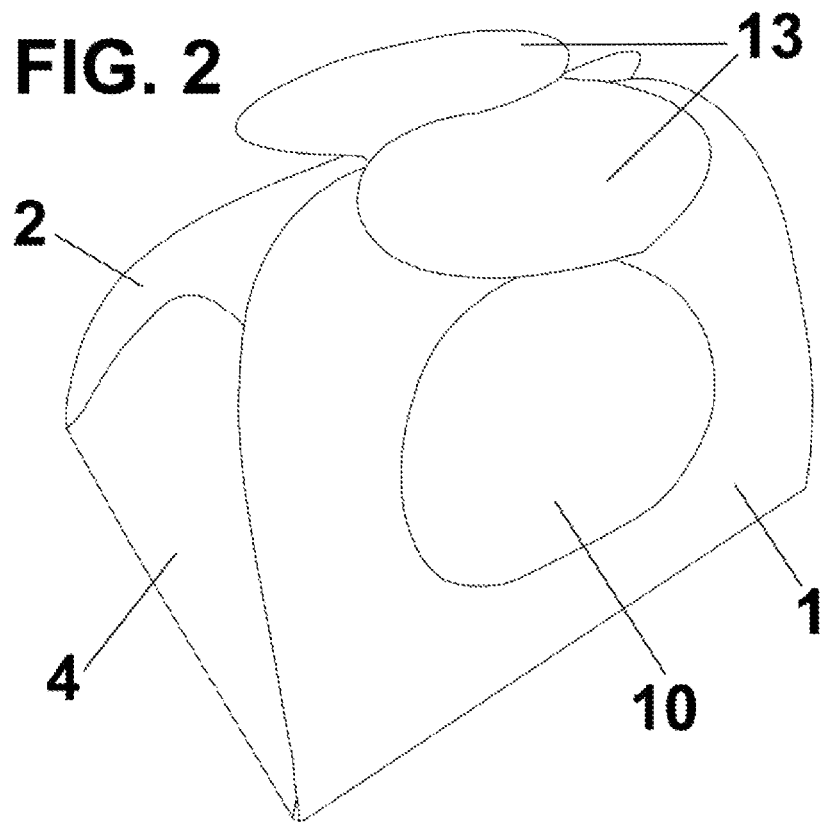
FIG. 2 is a perspective view of the volatile substance diffuser of the present invention according to the first embodiment, in its use position.
Figure 3:
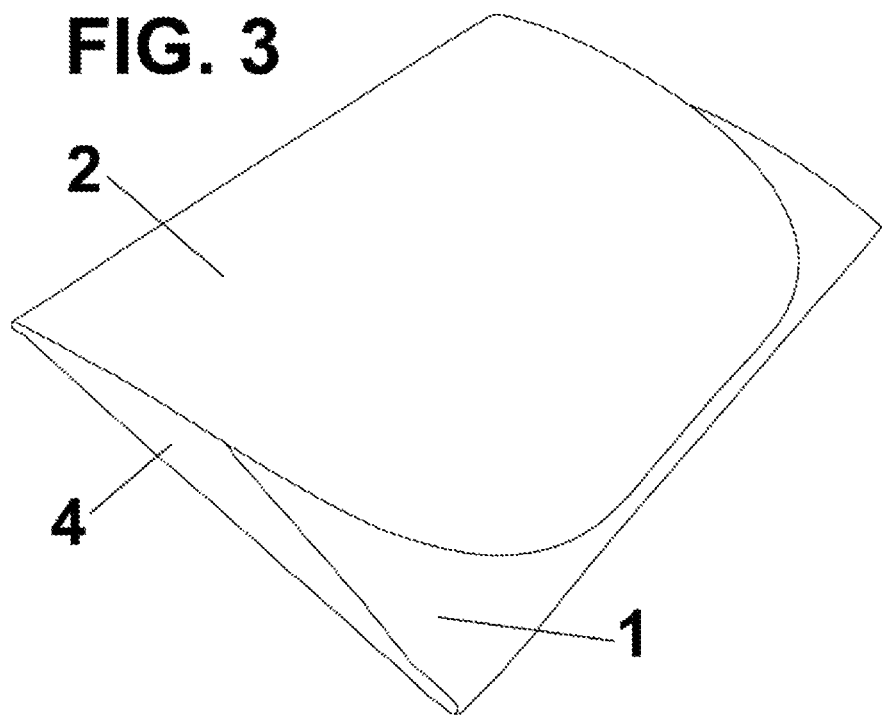
FIG. 3 is a perspective view of the volatile substance diffuser of the present invention according to the first embodiment, in its storage position.

FIGS. 1 to 3 show a first embodiment of the diffuser according to the present invention.

The volatile substance diffuser is formed from a sheet 11, for example made of cardboard, comprising a plurality of fold lines and a reservoir 10 containing the volatile substances.

The diffuser can be placed in a storage position (depicted in FIG. 3) and a use position (depicted in FIG. 2), as will be described below.

According to this first embodiment, the sheet 11 comprises a first face 1 on which the reservoir 10 is fixed, a second face 2 which serves to place the diffuser upright in its use position, a third face 3 provided with a hole 12 which serves to hang the diffuser for display, a fourth face 4 which also serves to place the diffuser upright in its use position, and a base face 5 which is used as a base in its use position.

Furthermore, the sheet 11 also comprises a pair of flaps 13, one being arranged on the first face 1 and one on the second face 2 for being coupled to one another to keep the diffuser stable in the use position, as shown in FIG. 2.

According to this first embodiment depicted in FIG. 1, said base face 5 is rectangular-shaped, although it could also be square-shaped, the first to fourth faces 1 to 4 extending from the sides of said base face 5.

The diffuser according to the present invention is sold in its storage position, depicted in FIG. 3, in which the first to fourth faces 1 to 4 are folded over the base face 5. In this position, the third face 3 can be unfolded so as to allow diffuser to be hung from a display.

For use, the first to fourth faces 1 to 4 are unfolded and are placed in their storage position, as shown in FIG. 2, and a sealing band 14 is removed from the reservoir 10 so as to allow diffusion of the volatile substances.

Figure 4:
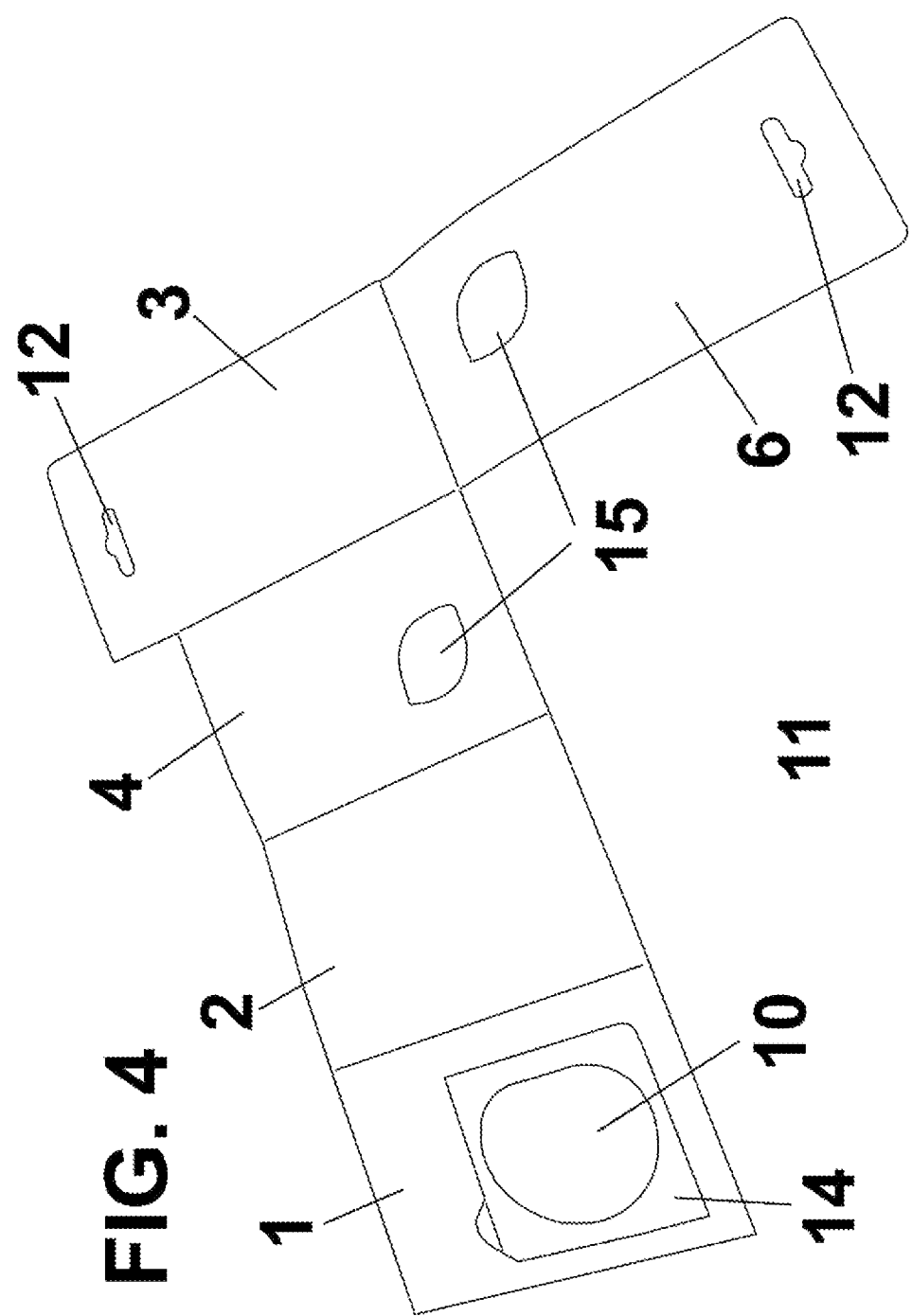
FIG. 4 is a perspective view of the unfolded sheet forming the volatile substance diffuser of the present invention, according to a second embodiment.
Figure 5:
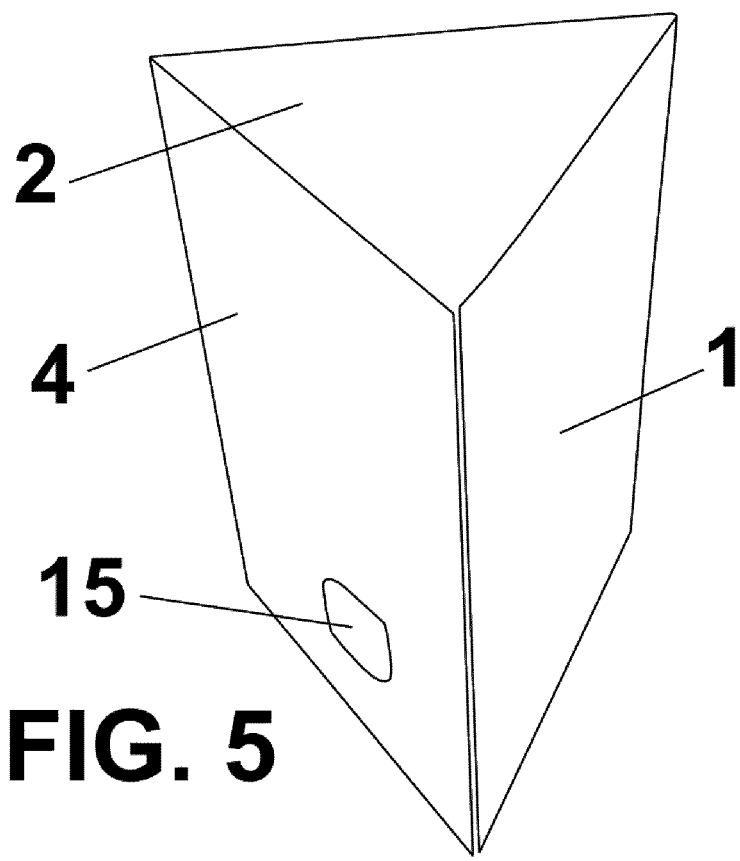
FIG. 5 is a perspective view of the volatile substance diffuser of the present invention according to the second embodiment, in its use position.
Figure 6:
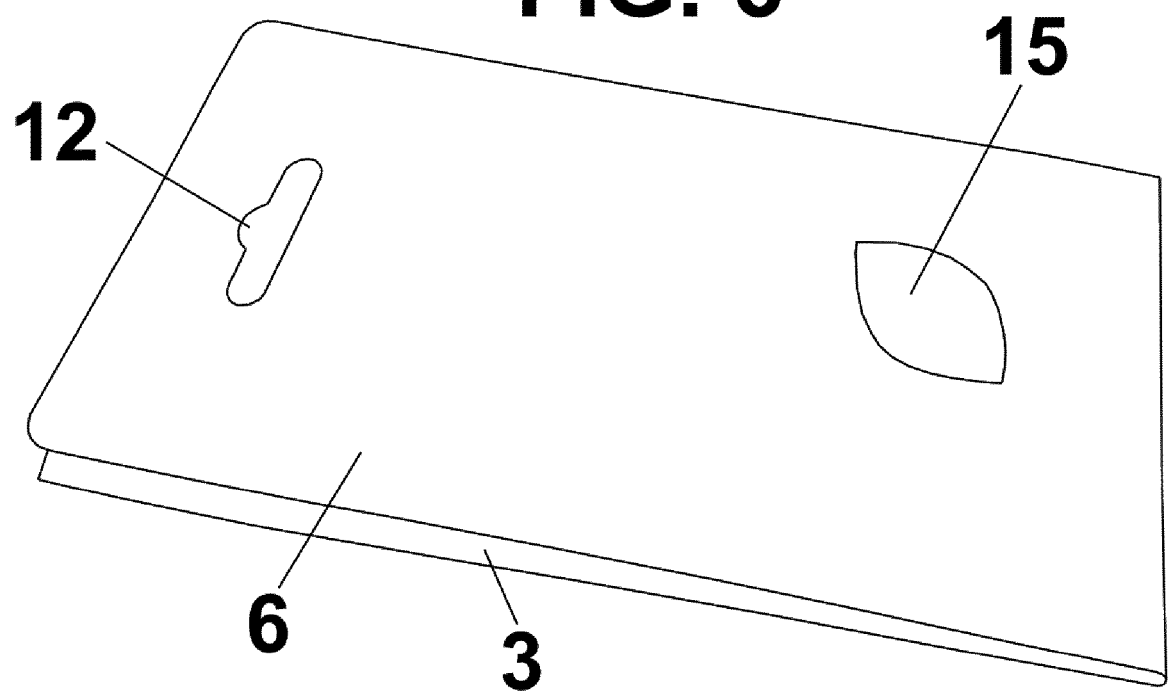
FIG. 6 is a perspective view of the volatile substance diffuser of the present invention according to the second embodiment, in its storage position.

FIGS. 4 to 6 show a second embodiment of the volatile substance diffuser according to the present invention. For the sake of simplicity and clarity, the same reference numbers are used to indicate the same components as in the first embodiment. Furthermore, the description of the elements performing the same function as in the preceding embodiment will not be repeated in detail.

In this second embodiment, the diffuser is also formed from a sheet 11 and a volatile substance reservoir 10.

Said sheet 11 comprises a first face 1 on which the reservoir 10 is fixed, a second face 2 which serves to place the diffuser upright in its use position, a third face 3 provided with a hole 12 which serves to place the diffuser for display, a fourth face 4 which also serves to place the diffuser upright in its use position, and a cover face 6 which is used to cover the third face 3 in the storage position of the diffuser.

This cover face 6 also preferably comprises a hole 12 for hanging the diffuser, as can be seen in FIG. 4, and this cover face 6 and the fourth face 4 may also comprise additional holes 15 for viewing the content of the reservoir 10 in the use position of the diffuser.

The arrangement of the faces of the sheet 11 in this embodiment is different from the preceding embodiment. As can be seen in FIG. 4, the first 1 face, second face 2, and the fourth face 4 are placed one after the other, while the third face 3 is separably attached to the fourth face 4 and the cover face 6 is attached to the third face 3.

The main difference between this second embodiment and the first embodiment is that the third face 3 is separated from the fourth face 4 before the first use of the diffuser, and accordingly the cover face 6 as well. To that end, the fold line which joins the third face 3 with the fourth face 4 is provided with a plurality of perforations to make this separation easier.

Once this third face 3 has been removed, the diffuser is placed in the use position as shown in FIG. 5, defining a triangular prism.

Although reference has been made to a specific embodiment of the invention, it is obvious for one skilled in the art that the volatile substance diffuser described is susceptible to a number of variations and modifications, and that all the mentioned details can be replaced with other technically equivalent details without departing from the scope of protection defined by the attached claims.

The invention claimed is:

1. A volatile substance diffuser, comprising a reservoir containing volatile substances, wherein the volatile substance diffuser is formed from a sheet provided with a plurality of fold lines, said sheet comprising:
    a first face on which said reservoir is fixed;
    a second face which supports the volatile substance diffuser upright in a use position together with said first face; and
    a third face provided with a hole for hanging the volatile substance diffuser;
    wherein:
    the first, second, and third faces of said sheet can be folded in a storage position;
    the sheet further comprises a cover face, which is folded over the third face and covers the entire third face in the storage position; and
    the first, second, third, and cover faces of the sheet can be completely unfolded from one another so that the sheet is in a laid-open, flat configuration in which the cover face is directly adjacent the third face.

2. The volatile substance diffuser according to claim 1, wherein said sheet further comprises a fourth face, which also supports the volatile substance diffuser upright in the use position.

3. The volatile substance diffuser according to claim 2, wherein said sheet further comprises a base face which forms a base of the volatile substance diffuser in the use position.

4. The volatile substance diffuser according to claim 1, wherein the first and second faces comprise respective flaps which are coupled to one another when the volatile substance diffuser is placed in the use position.

5. The volatile substance diffuser according to claim 3, wherein said base face is arranged in a centered position in said sheet and has a square or rectangular shape, said first to fourth faces extending from respective sides of said base face.

6. The volatile substance diffuser according to claim 2, wherein said first, second, and fourth faces are placed next to one another.

7. The volatile substance diffuser according to claim 1, wherein said third face is separable from the sheet when the volatile substance diffuser is placed in the use position.

8. The volatile substance diffuser according to claim 1, wherein said cover face is attached only to said third face.

9. The volatile substance diffuser according to claim 1, wherein said reservoir comprises a separable sealing band which is removed before a first use of the volatile substance diffuser.

10. The volatile substance diffuser according to claim 1, wherein said sheet is made of cardboard.

* * * * *